United States Patent [19]

Doorenbos et al.

[11] Patent Number: 4,672,136

[45] Date of Patent: Jun. 9, 1987

[54] MONOADDUCT MONOMERS AND POLYADDUCT POLYMERS FROM DIVINYL KETONES

[75] Inventors: Harold E. Doorenbos; Giffin D. Jones, both of Midland, Mich.

[73] Assignee: The Dow Chemical Company, Midland, Mich.

[21] Appl. No.: 813,327

[22] Filed: Dec. 24, 1985

[51] Int. Cl.$^4$ .............................................. C07C 145/00
[52] U.S. Cl. ......................................... 558/61; 544/399
[58] Field of Search .................... 260/513.7, 239 E; 558/61, 156, 253; 568/64; 564/502; 546/233; 526/268

[56] References Cited

U.S. PATENT DOCUMENTS

| | | | |
|---|---|---|---|
| 2,105,792 | 1/1938 | Nelles | 260/134 |
| 2,212,150 | 8/1940 | Burke | 568/63 |
| 2,427,582 | 9/1947 | Vinton | 558/253 |
| 2,522,670 | 9/1950 | Frank | 568/63 |
| 4,246,386 | 1/1981 | Howell | 526/207 |
| 4,401,742 | 8/1983 | Chiang | 430/137 |
| 4,456,643 | 6/1984 | Colyer | 428/643 |
| 4,460,477 | 7/1984 | Costello et al. | 210/701 |
| 4,477,644 | 10/1984 | Sutton et al. | 528/73 |
| 4,510,059 | 4/1985 | Amjad et al. | 210/701 |

FOREIGN PATENT DOCUMENTS 1421597  1/1976  United Kingdom .

OTHER PUBLICATIONS

CA42:7727i; 7729i; 7738d; 7739c (1948), Nazarov & Coworkers.
CA43:6625a (1949), Nazarov & Coworkers.
CA58:7819h (1962), Ivanova et al.
Mirinov et al., *J. Gen. Chem. USSR*, 33(5), 1476–1480 (1963).
CA65: 13834h (1966) Takemoto et al.
*Kogyou Kagahu Zasshi*, 69, 524–526 (1966).
Reed, *J. Org. Chem.*, 27, 4116–4117 (Nov. 1962).

*Primary Examiner*—Paul R. Michl
*Assistant Examiner*—Alex H. Walker

[57] ABSTRACT

Included are monoadduct monomers made from divinyl ketones wherein only one vinyl bond therein has added to it a nucleophilic precursor. Nucleophilic precursors include phenols, thiols, secondary amines, amino acids, hydrocarbyl phosphites and phosphite esters, organic bis(phosphonites, the bisulfite anion and others.

Polyadduct polymers made from the monoadduct monomers. The polyadduct polymers may be homo- or copolymers and may contain a pendant nucleophile residue.

24 Claims, No Drawings

MONOADDUCT MONOMERS AND POLYADDUCT POLYMERS FROM DIVINYL KETONES

FIELD

This invention relates to monomers and prepolymers from divinyl ketones. It also relates to polymers from divinyl ketones.

BACKGROUND

Certain addition reactions and products of certain divinyl ketones are known. Divinyl ketones have known polymerization capability.

British Pat. No. 1,421,597 (1976) (incorporated herein by reference) teaches the sizing of paper using mono-olefinically unsaturated comonomers containing one or more tertiary or quaternary nitrogen atoms such as mono-olefinically unsaturated carboxylates, 1-diethylamino-4-penten-3-one and 1-[N-(2-chloro-3-hydroxypropyl), 0-formyl-morpholinium]-4-penten-3-one. No methods were disclosed to prepare these comonomers.

Nazarov and various coworkers, CA 42:7727i; 7729i; 7738d; and 7739c (1948); and CA 43:6625a (1949) (each abstract incorporated herein by reference), teach the addition of aniline; malonic ester, acetoacetic ester and acetylacetone; hydrogen sulfide; alcohols; and hydrogen cyanide, respectively, to 5-methyl-1,4-hexadien-3-one. The addition was to the 1-ene bond in forming the straight-chain addition products. Hydrogen sulfide addition resulted in formation of 2,2-dimethyltetrahydro-1,4-thiapyrone.

Ivanova et al., CA 58:7819h (1962) (abstract incorporated herein by reference), teach the addition of an alkyl nitroamino group to the 1-ene bond of 5-methyl-1,4-hexadien-3-one and 1,4-hexadien-3-one.

Mirinov et al., *J. Gen. Chem. USSR*, 33(5), 1476–1480 (1963) (pages incorporated herein by reference), teach the preparation of certain 1-(diethylamino)-4-penten-3-one and 1-diethylamino-5-methyl-4-hexen-3-one by the hydrochloric acid catalyzed Mannich reaction of diethylamine hydrochloride, formalin and methyl ethyl ketone at 100° C. The preparation of divinyl ketones based on the Mannich reaction is also taught.

Takemoto et al., CA 65:13834 h (1966) and *Kogyo Kagahu Zasshi*, 69, 524–526 (1966) (abstract; and pages incorporated herein by reference), discuss the reaction of divinyl ketone with thiophenol, thioacetic acid, thiolbenzoic acid, aniline, piperidine, malononitrile and hydroxylamine. Both vinyl bonds in the divinyl ketone became saturated upon the addition of these compounds.

In addition, certain polymeric materials derived from divinyl ketones are known. It is known to employ the compound divinyl ketone (i.e., 1,4-pentadien-3-one) in certain polymerizations and as a cross-linker in certain polymeric materials.

For example, Chiang, U.S. Pat. No. 4,401,742 (1983) (incorporated herein by reference), teaches that divinyl ketone may be used as a monomer in the polymerization of a polymer used as a matrix to support pigmentive particles in a copying machine as a toner.

Castello et al., U.S. Pat. No. 460,477 (1984) and Amjad et al., U.S. Pat. No. 4,510,059 (1985) (both incorporated herein by reference), teach that unspecified divinyl ketones may be copolymerized with a cationic-containing monomer to make polyampholytes useful as cationic polymers or surfactants for silica scale inhibition in brines.

Howell et al., U.S. Pat. No. 4,246,386 (1981) and Colyer, U.S. Pat. No. 4,456,643 (1984) (both incorporated herein by reference), teach that divinyl ketone may be used in free radical copolymerizations with other vinyl resins to obtain a cross-linked vinyl copolymer useful as crush-resistant beads and as an ion-exchange resin support (Howell et al.) and sealant coating of a fibrous backing to a decorative laminate useful as a floor covering (Colyer).

What is lacking in these patents and publications and what is needed are certain monoadduct monomers from divinyl ketones and a process to prepare monoadduct monomers from divinyl ketones efficiently. What is additionally lacking in these patents and publications and what is needed are certain polyadduct polymers, especially as novel easily cured coatings and more especially from the monoadduct monomers or A- or B-stage resins derived from compounds such as divinyl ketones.

SUMMARY

In one aspect, the invention is a process for preparing monoadduct monomers of divinyl ketones comprising contacting a nucleophilic precursor with a divinyl ketone under conditions sufficient to prepare the monoadduct monomer. Another aspect of the invention comprises compositions of the monoadduct monomer produced.

An additional aspect of the invention is a polyadduct polymer comprising polymer linkages resulting from self-addition of a monoadduct monomer of a divinyl ketone. Further aspects of the invention include a method of preparing the polyadduct polymers and methods of using the polyadduct polymers.

The monoadduct monomers are useful in homopolymerizations and in copolymerizations. Sulfur-containing monoadduct monomers and their Se and Te analogues are useful as biologically-active agents and in vulcanizations. The monomer often must be substantially free of the divinyl ketones as small amounts of unconverted divinyl ketones can cause unwanted cross-linking in certain later polymerizations, and the process of the invention prepares such a monomer.

The polyadduct polymers may be used in sewage filtration, as coatings and flame retardants, for example, as the particular polymeric product admits. Sulfur-containing polyadducts may be additionally especially used as biologically active agents and in vulcanizations. The polyadduct polymers preferably have high thermal stability, plus toughness and adhesion to solid surfaces, especially to metals.

DETAILED DESCRIPTION

Divinyl ketones include $\alpha\beta$-diethylenically unsaturated ketones of the general formula

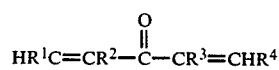

wherein $R^1$, $R^2$, $R^3$ and $R^4$ include separately in each occurrence hydrogen or methyl, provided that when $R^1$ is hydrogen so is $R^4$.

More preferably, at least $R^2$ and $R^3$ are both hydrogen or both methyl, especially both hydrogen. Most preferably, at least $R^1$ and $R^4$ are both hydrogen. The most especially preferred of the divinyl ketones is the compound divinyl ketone.

The divinyl ketones are commercially available or may be prepared by methods known in the art. For example, many divinyl ketones, including the compound divinyl ketone, may be prepared by the method taught by Nelles, U.S. Pat. No. 2,105,792 (1938) (incorporated herein by reference), or by the method of Mirinov et al. Additionally, divinyl ketone may be prepared by the method of Reed, *J. Org. Chem.*, 27, 4116–4117 (November, 1962) (incorporated herein by reference).

The nucleophilic precursor is a compound which is sufficiently nucleophilic to add across a carbon to carbon double bond (vinyl bond) of the divinyl ketone. The nucleophilic precursor may be a separable monoadduct monomer precursor. By separable is meant that, upon the addition, the nucleophilic precursor separates into independent moieties which add to either the α-carbon or to the β-carbon of one of the vinyl bonds of the divinyl ketone. Vinyl bond herein refers to an α, β-carbon to carbon double bond of the divinyl ketones or monoadduct monomers. The nucleophilic precursor is preferably of the general formula $Q(H)_n$ wherein at least one hydrogen or the equivalent is donated by it to the vinyl group of the divinyl ketone. Examples include the hydrogen of a secondary amino group, the hydrogen of a chalcogen-containing nucleophilic precursor such as a thiol, the hydrogen of a bisulfite ion or from a phosphite ester in the presence of a protic solvent component. In this last case, the adding group

comes from the trisubstituted phosphite and the hydrogen from the protic solvent.

The nucleophilic precursors include electron-rich moieties. Preferable examples include nitrogen-containing compounds such as secondary amines (including imines and secondary amino-containing polyvalent amines with otherwise blocked non-secondary amino groups) like dimethylamine, methylethylamine, dibutylamine, N-ethylcyclohexylamine, N,N'-dimethylethylenediamine, N,N'-dimethylethylenediamine monoacetate, aziridine, piperazine, $C_{1-20}$ hydrocarbyl, hydroxy or $C_{1-20}$ oxyhydrocarbyl-substituted piperazines and combinations thereof, N-methylpiperazines, N-ethylpiperazines, 1-piperazineethaneamine monoacetate, 3,3-dimethylazetidine, perhydropyridine, N-methylaniline; organophosphorous compounds like phosphite esters and alkyl, aryl, arylalkyl and alkylaryl phosphites, and combinations of these moieties such as in a hydrocarbylenebis(phosphonite); arsenic analogues of these; oxygen-containing compounds such as phenols; mercapto compounds like thiols such as thiomethanol (i.e., methyl mercaptan), thioethanol, thiophenol and polythiols; other chalcono compounds (i.e., Se, Te) analogous to the mercapto compounds; anions like bisulfite (e.g., sulfite in aqueous solution also), mono- and polysulfinic acids, sulfinic acid salts (e.g., base catalyzed) and thiocarboxylic acids like thioacetic acid and thioesters thereof; selenium and tellurium analogues of the foregoing; halides (i.e., fluoride, chloride, bromide, iodide, triiodide), mixed halides, psuedohalides (e.g., cyanide, chalconocyanides, cyanate, chalconocyanates, chalcogens therein being sulfur, selenium and tellurium), especially as in aqueous solution, weak monoprotic acids such as prussic and the like; mixed moiety compounds such as oxazoles, oxamines, hydroxylamines like diethanolamine, thiazoles or thiamines, for example, amine crown ethers and chalconoethers like mono- and poly-secondary amine crown ethers and thioethers such as N,N'-bis(1-methylethyl)-9-thiabicyclo[3.3.1.]nonane-2,6-diamine, amino acids such as histidine and cysteine, phosphorous/sulfur compounds, phosphorus/nitrogen compounds; and the like.

The nucleophilic precursor may be charged such as in $HSO_3^-$. When charged, a counter-ion, such as $Na^+$, accompany it.

Substituted piperazines are preferred nucleophilic precursors and are a preferred class of nitrogen/carbon heterocycles with secondary amino functionality and include compounds of the formula

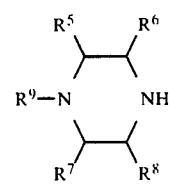

wherein $R^5$, $R^6$, $R^7$ and $R^8$ are each independently hydrogen, methyl, hydroxymethyl, 1- or 2-hydroxyethyl or the like; and $R^9$ is independently hydrogen, hydroxy or $C_{1-20}$ organic.

Preferably, $R^{5-8}$ are each independently hydrogen or methyl and most preferably hydrogen. More preferably, $R^9$ is hydrogen, $C_{1-4}$ alkyl or $C_{1-4}$ aminoalkyl and most preferably hydrogen or $C_{1-4}$ terminal aminoalkyl. An example of a most preferred substituted piperazine is 1-piperazineethaneamine.

Organic bis(phosphonites) are preferred nucleophilic precursors and are a preferred class of the organophosphorus compounds and include compounds of the formula

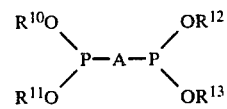

wherein each of $R^{10-13}$ is independently $C_{1-10}$ alkyl, aryl, arylalkyl or alkylaryl, and A is an organic moiety, preferably an aromatic organic moiety to which the phosphorus atoms are bonded because of greater intramolecular stability. Preferred aromatic A-moieties (with attached phosphorous) include arylenebis(phosphonites) which include substituted variants such as $C_{7-15}$ arylalkylbis(phosphonites). Preferred arylenebis(phosphonites) include substituted p-phenylenebis(phosphonites) such as compounds of the formula:

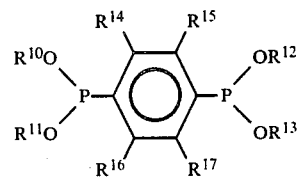

wherein $R^{10-13}$ is as defined above and each of $R^{14-17}$ is hydrogen or methyl, hydroxymethyl, (1- or 2-hydroxyethyl) or the like; and o- and m-P variants thereof. Preferably, each $R^{14-17}$ is independently hydrogen or methyl. Also preferred are arylenebis(phosphonites) of the formula:

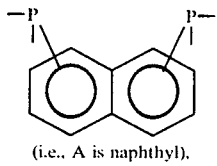
(i.e., A is naphthyl),

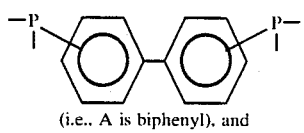
(i.e., A is biphenyl), and

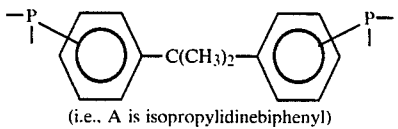
(i.e., A is isopropylidinebiphenyl)

and ring-substituted variants thereof, especially those substituted variants with alkoxy moieties on the rings such as para-methoxy substitutions and other variants similar to the substituted phenylenebis(phosphonites).

Preferred A-moieties also include organic aromatic moieties such as

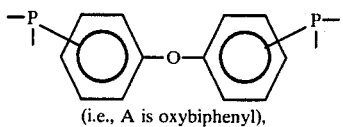
(i.e., A is oxybiphenyl),

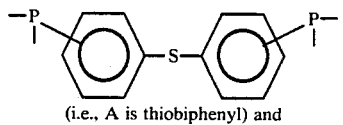
(i.e., A is thiobiphenyl) and

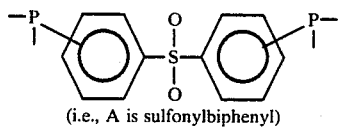
(i.e., A is sulfonylbiphenyl)

and ring-substituted variants thereof, especially ubstituted variants with alkoxy moieties on the rings such as para-methoxy substitutions and other variants similar to the substituted phenylenebis(phosphonites).

A most especially preferred A-moiety is para-phenylene. An example of a most especially preferred arylenebis(phosphonite) is tetramethyl 1,4-phenylenebis(phosphonite).

Secondary amine crown chalconoethers are a preferred class of nucleophilic precursors having exclusive active aliphatic secondary amino functionality and include compounds of the formula

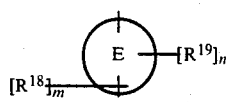

wherein the circle represents a $C_{3-12}$ carbon ring;

E represents oxygen or sulfur and is connected to the ring either directly or through a $C_{1-7}$ crown alkyl chain connected to the ring;

$R^{18}$ pertains to moieties bonded to the ring or the crown chain and is independently for each occurrence hydrogen or a $C_{1-10}$ hydrocarbyl group which may be interconnected and attached in multiple locations;

$R^{19}$ is independently for each occurrence a $C_{1-10}$ alkyl or aryl secondary amino group;

m is a non-negative integer of the valence of the ring minus n; and n is an integer from zero up to and including 5.

The secondary amine crown chalconoethers may be prepared by known methods such as by the method of Sutton et al., U.S. Pat. No. 4,477,644 (1984) (incorporated herein by reference). Oxygen may be substituted for sulfur therein by known methods.

Preferably, the carbon ring of the secondary amine crown chalconoether is alkyl; E is sulfur and is connected to the ring directly; $R^{18}$ is independently for each occurrence hydrogen or up to and including four $C_{1-4}$ alkyl groups each attached in one location; $R^{19}$ is $C_{1-4}$ alkyl secondary amino; and n is 1 or 2. More preferably, the carbon ring is $C_{6-10}$ alkyl, and $R^{18}$ is exclusively hydrogen. A most preferred secondary amine crown chalconoether is N,N'-bis(1-methylethyl)-9-thiabicyclo[3.3.1.]nonane-2,6-diamine.

More preferred nucleophilic precursors are sulfinic acids and esters and thiocarboxylic acid esters of about 20 carbon atoms or less per acid and of about 10 carbon atoms or less per ester moiety; compounds having exclusive active mercapto functionality of about 20 carbon atoms or less such as thioethanol, thiophenol, thioacetic acid, (1,1'-biphenyl)-4,4'-dithiol and 4,4'-thiobis(benzenethiol); compounds having exclusive active aliphatic secondary amino functionality of about 20 carbon atoms or less, such as dimethylamine, diethylamine, N-ethylcyclohexylamine, aziridine and N-methylaniline, piperazine, 2,6-diethyl-3,5-dimethylpiperazine, N-methylpiperazine, piperazine monoacetate, 1-piperazineethaneamine monoacetate; aromatic bis(sulfinic) acids such as 1,4-phenylenebis(sulfinic) acid or the corresponding 4,4'derivatives of biphenyl or diphenyl ether; secondary amine crown ethers and thioethers (i.e., E is oxygen or sulfur) such as N,N'-bis(1-methylethyl)-9-thiabicyclo[3.3.1.]nonane-2,6-diamine and the like; the bisulfite anion; phosphite esters of about 10 carbon atoms or less per ester moiety; and arylenebis(phosphonites) of the formula $(R^{10-13}O)_2P-A-P(OR^{10-13})_2$ wherein each of $R^{10-13}$ is independently $C_{1-10}$ alkyl, and A is $C_{7-15}$ arylalkyl or ortho-, meta- or para-phenylene, naphthylyl, biphenyl, methylenebiphenyl or isopropylidinebiphenyl, or oxybiphenyl, thiobiphenyl or sulfonylbiphenyl.

Most preferably, the nucleophilic precursor is monovalent (i.e., n=1). Examples of most preferable nucleophilic precursors are dimethylamine, N-ethylcyclohexylamine, N-methylaniline, monovalent nitrogen/carbon heterocycles with aliphatic secondary amino functionality, N-methylpiperazine, 1,2,3,5-tetramethyl-1-piperazineethaneamine monoacetate, N,N'-dimethylethylenediamine monoacetate, monovalent aliphatic mono- and poly-secondary amine crown ethers and thioethers of about 20 carbon atoms or less, aziridine, the bisulfite anion such as found in conjunction with a cation, especially an alkali metal cation like sodium, and monophosphite esters of about 10 carbon atoms or less per ester. The aromatic organic bis(phosphonites) are slow to react unless in the presence of strong base.

Especially preferred are dimethylamine, aziridine, 1-piperazineethaneamine monoacetate, N,N'-bis(1-methylethyl)-9-thiabioyclo[3.3.1]nonane-2,6-diamine monoacetate, the bisulfite anion, para-phenylene-bis(-dimethoxyphosphonite) and trimethylphosphite.

Hydrogen sulfide, ammonia and unblocked primary amines cause cyclization with the divinyl ketones and are not by themselves suitable nucleophilic precursors of this invention. However, a primary amine group may be blocked by such cyclization reaction with the divinyl ketones. For example, the primary amino-group of 1-methylamino-2-aminoethane (i.e., N-methylethylenediamine) may cyclize with a divinyl ketone (i.e., both vinyl bonds of the divinyl ketone become saturated upon the cyclization addition), becoming blocked with the secondary amino-group a suitable nucleophilic precursor, thus making this cyclic-blocked compound a suitable nucleophilic precursor of the invention. Ammonia may cyclize into a secondary amine. Tertiary amine and amino salt groups do not react appreciably and are considered blocked herein.

The tendency of polyvalent ionic precursors is to form oligomeric and polymeric monoadduct monomers at equivalent concentrations of the polyvalent nucleophilic precursor and reactant divinyl ketones. These can be controlled by nominally blocking the unwanted valent groups such as by acidifying, preferably with a weak acid such as acetic, propionic and the like. In this manner, polyvalent amines, including polyvalent amines having otherwise primary amino groups in conjunction with secondary amino groups, may be blocked to reduce the valence of the amine, and/or block the functionality of the primary amino group, allowing the desired number of valent secondary amino groups to react as the functionality of the nucleophilic precursor as a secondary amine herein. Thus, a potentially polyvalent nucleophile may be considered monovalent by blocking.

Preferably, if blocked in situ, the selectivity to the desired blocked form is about 50 percent or above, more preferably about 80 percent or above, most preferably about 90 percent or above, and especially about 95 percent or above.

It is also preferred that the nucleophilic precursor is such that in an unblocked state, it has a valence of from 2 to 5, and is blocked to a valence of 1. More preferably, such blocking is from an unblocked di- or trivalent state, most preferably from an unblocked divalent state. It is especially preferred therein that these blocked moieties are secondary amine functionalities. An example is 1-piperazineethaneamine blocked to 1-piperazineethaneamine monoacetate.

The nucleophilic precursor and the divinyl ketone(s) are contacted under conditions sufficient to prepare the monoadduct monomer. Preferably, the monoadduct monomers prepared include compounds of the general formula

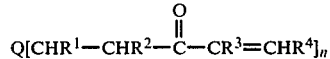

wherein
Q is a nucleophile residue of an n-valent nucleophilic precursor;

wherein $R^1$, $R^2$, $R^3$ and $R^4$ are as previously defined herein; and n is a natural number up to about 5 which is the valence of the nucleophilic precursor.

Preferably, $R^1$, $R^2$, $R^3$ and $R^4$ are in each occurrence hydrogen or methyl, more preferably at least $R^2$ and $R^3$ are both hydrogen or both methyl, especially both hydrogen. Most preferably at least $R^1$ and $R^4$ are both hydrogen because of ready copolymerization capability. It is especially preferred that each of $R^1$, $R^2$, $R^3$ and $R^4$ is hydrogen.

Monoadduct in monoadduct monomers herein refers to the adding to the divinyl ketones. It necessarily involves only one of the vinyl bonds of the divinyl ketones. For example, the addition product of 2 divinyl ketones to one 1,2-dimethylaminoethane is a monoadduct monomer.

The monoadduct monomer produced may be present in a state which is preliminary to, or may even be considered as, a state such as B-stage resin. A state such as a B-stage resin means a state in which the monoadduct monomer product is only partially soluble in a $C_{1-6}$ organic diluent. A state preliminary to a state such as a B-stage resin may include a state such as an A-stage resin. A state such as an A-stage resin means a state in which the monoadduct monomer product is generally soluble in a $C_{1-6}$ organic diluent.

The nucleophilic precursor and the divinyl ketone(s) may be contacted neat or in a diluent such as liquid alkanes like liquid propane and hexanes, other hydrocarbons like toluene and benzene, halogenated hydrocarbons like fluorocarbons and methylene chloride, hydroxylated hydrocarbons like aliphatic alcohols and polyols especially alkyl alcohols, ethers like diethyl ether and tetrahydrofuran, or water. The nucleophile need not be soluble in the water or organic diluent but preferably is $C_{1-4}$ alkyl alcohols, such as methanol, ethanol, isopropanol and t-butanol and water are preferred diluents. Water and $C_{1-4}$ primary alkyl alcohols are more preferred diluents. Water and the $C_{1-4}$ primary alcohols are independently preferred from each other. The alcohols are especially preferred to work up the organic bis(phosphonites) into the monoadduct monomer which preserves an unhydrolyzed phosphorus moiety. Water is the most preferred diluent.

Preferably, the diluent is employed to dissolve all reactants and any added promoter. Either or both of the reactant components may advantageously be diluted or solvated prior to reaction, if desired. Solvation or dilution may also be carried out during or after reaction.

Preferably, the divinyl ketones are present in excess of the nucleophilic precursor based on the valence of the precursor. The excess is to avoid diadduct formation. By valence of the precursor is meant the potential l number of bonds that the precursor could form with single molecules of the divinyl ketone, assuming a monoadduct monomer is produced. The valence of the nucleophilic precursor does not include blocked or otherwise nonreactive groups. Thus, the valence of the bisulfite anion and dimethylamine is one each. The valence of 1-piperazineethaneamine monoacetate is nominally one. The valence of N,N'-dimethylethylenediamine and piperazine is two each. Thus, an equimolar ratio based on one mole of the divinyl ketone would require one mole of a monovalent precursor such as the bisulfite anion. An equimolar ratio based on one mole of the divinyl ketone would require one-half mole of a divalent nucleophilic precursor such as piperazine. An excess would require more than one mole of the divinyl ketones as just illustrated.

Preferable molar ratios of the excess are about 1.1 or above as in a batch process at completion. More preferably, the excess as in a batch process at completion and before removal of the excess has the molar ratio maximum of about 5.

The nucleophilic precursor may be advantageously added slowly to the divinyl ketone, especially in a batch process. Flow reactor methods may be advantageously used also, especially to maintain the desired excess.

In addition to control by blocking, unwanted oligomeric and polymeric monoadduct monomers can also be controlled by the reaction temperature. Temperature of reaction is generally about 80° C. or below, preferably about 50° C. or below and more preferably about 30° C. or below. The temperature is kept lower to avoid contributing to the formation of diadduct monomer, premature polymerization products and tars, such as formed when methylene bisacrylamide adds bisulfite at about 70° C. Too low a temperature may slow the reaction to undesirable rates.

The reaction may be exothermic to a greater or lesser extent. Therefore, the temperature may be advantageously controlled by heat exchange from the reacting system to the external environment, if necessary.

Pressure of the reaction is preferably ambient atmospheric or below. Reduced pressures above the liquid phase may aid in removal of the unreacted divinyl ketones or other volatiles such as a volatile solvent.

The reaction may be, and preferably is, carried out in the dark. More preferably, the vessel protects the reaction system from UV and visible light and any other electromagnetic radiation which might be actinic. An example of such other radiation could be a microwave flux which might heat the reacting system to an unwanted degree, especially if water is present.

The reaction is best run under partially neutralized conditions. By partially neutralized is meant that the formation of the monoadduct monomer is not generall catalyzed by a protic acid or the like. Thus, for example, in an aqueous reaction system wherein the bisulfite ion is being added, the pH will usually be above about six. Preferably, for nucleophilic precursors generally considered polyvalent like piperazine, the operating pH is about one unit higher than the lowest $pK_a$ of the precursor in the reaction medium employed.

The reaction may be, and preferably is, base promoted. Preferable base promoters are, in addition to the basic nucleophilic precursors themselves, tertiary alkylamines and hydroxide ions. Nucleophilic precursors which are less reactive (i.e., have less nucleophilic precursor character) such as phenols and the organic bis(phosphonites) and other phosphite esters may require a stronger base such as an alkoxide of an alkali metal such as sodium.

More preferably, base promoters are present as measurable ions at a concentration range of from about $1 \times 10^{-7}$ molar to about $1 \times 10^{-4}$ molar. Thus, in water, a more preferable pH is from about pH 7 to about pH 10. Very high measurable concentrations of base-promoting ions may contribute to unwanted cleavage of the monoadduct monomer, for example, by a process such as by hydrolysis. A more neutral pH may be advantageously employed when a polyvalent nucleophilic precursor such as piperazine is blocked by acidifying unwanted valent groups such as in piperazine monoacetate and reacted in the blocked form as a monovalent secondary amine.

Phosphorus esters and the like nucleophilic precursors (e.g., the organic bis(phosphonites) upon reacting form a monoadduct monomer wherein the phosphorus or the like reacts with the divinyl ketones in the following exemplary manner:

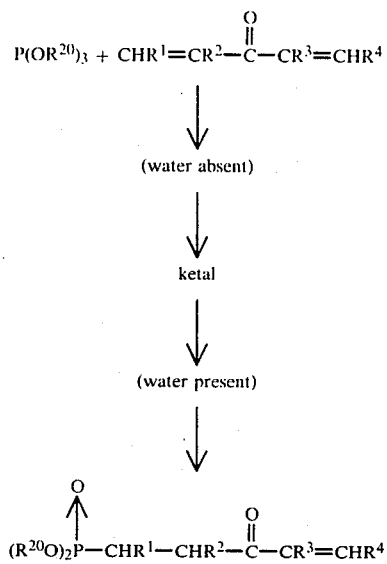

wherein $R^{20}$ is independently each occurrence inclusive of $C_{1-10}$ alkyl or aryl. The hydrogen in the monoadduct monomer thus comes from the aqueous contact in this case. Preferably, phosphite esters are contacted with the divinyl ketones in the presence of a strong base, such as alkoxides, or at a high base concentration such as measured by the equivalent of aqueous pH such as above about 10, in an alcohol solvent.

Bisulfite is preferably added in dilute solution, maintaining the pH or equivalent measure thereof between about 7 and 11. Bisulfite is added incrementally so that the pH does not rise above about 11 and any heat generated is easily dissipated. With each addition of bisulfite, the pH drops off; then rises again. More bisulfite is then added. Preferably, the pH therein is maintained between about 8 and 10. Most preferably, water is the solvent. The monoadduct monomer formed is typically an anion.

The reaction is carried out until the desired level of completion is accomplished. Often, the time of completion based on limiting reagent and equilibrium considerations is short, preferably about one hour or less and more preferably about one-half hour or less.

The monoadduct monomer is collected (i.e., separated from reactant mixture) by methods known in the art. Often, the monoadduct monomer is found as a liquid under normal laboratory conditions of temperature and pressure. The monoadduct monomer may be a solid. Thus, the preferred separation methods include chromatographic methods such as gel, gel electrophoresis, ion-exchange, high pressure liquid and thin layer chromatography and also include extraction and distillation of any excess reactant.

In a solvent system comprising polar liquids, especially $C_{1-4}$ primary alkyl alcohols or water, more preferred methods of collection are extraction and distillation of any excess reactant. Preferred extractants therein are the hydrocarbons and halogenated hydrocarbons which can be used as solvents and are immiscible therewith. More preferably, they are liquid under normal laboratory conditions. A most preferred aqueous extractant is methylene chloride.

Each method, extraction and distillation, is separately preferred. Often distillation can be more advantageous when the excess reactant is more volatile than the product, as can be the case in systems like the batch reaction of basic, aqueous sodium bisulfite added dropwise to the compound divinyl ketone. Distillation may also be advantageous in removal of other volatiles.

It is often desired to obtain monomer free of cross-linking agent in order that it can be polymerized or copolymerized to a fully soluble high molecular weight polymer or copolymer and used, for example, as an enhanced oil recovery agent. It is readily possible to achieve this result by using the divinyl ketone in excess and removing and recovering the excess by distillation, along with some of the water, from the non-volatile monoadduct solution. Alternatively, one can extract the divinyl ketone, for example, with methylene chloride.

If it is desired to separate the monoadduct from a bis-adduct, one can do so by chromatographic or crystallization methods but these are more expensive, and it is not necessary to do so for the purpose of making an enhanced oil recovery agent. The bis-adduct acts as an additive.

A polymerization inhibitor may be employed. Examples are sodium nitrite, sodium picrylsulfonate and diphenylamine. Preferred concentrations of the inhibitors are from 1 percent to 10 percent by weight. At higher temperatures, more inhibitor may be present. However, such an inhibitor may affect any polymerized product from the monoadduct monomer and may have to be removed or rendered inactive. Preferred removal techniques include solvent extraction and ion-exchange chromatography. For example, it may be advantageous to extract diphenylamine by a water-immiscible aprotic solvent in cases where the monoadduct monomer is dissolved in an aqueous medium. It may be advantageous to remove sodium picrylsulfonate by ion-exchange chromatography.

The monoadduct monomer may be advantageously stored away from base or peroxide contact in a closed vessel, cooled preferably to about 10° C. or below, under a dry gas such as argon or nitrogen and kept away from actinic radiation. It may then be used at a later time. Alternatively, the monoadduct monomer may be used directly after its preparation, with or without additional purification, as desired.

The most advantageous methods of polymerizing the monoadduct monomers are free radical initiated and base catalyzed condensation polymerization. Often gentle heating alone is sufficient.

The prepared monoadduct monomers are useful in both homopolymerizations and copolymerizations. For example, the monoadduct monomer from the nucleophilic precursor bisulfite anion is advantageously copolymerized in an acrylamide copolymer as an agent for viscous oil drive in calcium-containing water. The monoadduct monomer from 1-piperazineethaneamine can be used as a flocculant, especially in acid slimes.

The amino-containing monoadduct monomers are especially useful as polymerized dewatering agents for sewage solids, for example. The oxygen-containing monoadduct monomers, such as obtained from bisphenol A are useful in often transparent coatings after gentle heating, preferably with base promotion. The thio-containing monoadduct monomers are especially useful as bioactive agents and as a monomer for a cured coating, also after gentle heating and preferably with base promotion. The mixed nitrogen/chalcogen-containing monoadduct monomers are similarly useful and similarly prepared.

The monoadduct monomers prepared from phosphorus-containing nucleophilic precursors, especially phosphite esters, are especially useful as flame retardants. They are more especially useful as from a phosphite ester precursor when the monoadduct monomer has been treated with a basic protic solvent which forms in such case a sodium cation compound with the phosphorus (IV), releasing the corresponding hydroxy-containing cation compound such as methanol in the case of the phosphite ester nucleophilic precursor trimethyl phosphite. These flame retardants are advantageously simply added to an otherwise more flammable fabric like cotton.

The polyadduct polymer comprises polymer linkages resulting from self-addition of a monoadduct monomer of a divinyl ketone. The polymer linkages are preferably moieties of the general formula

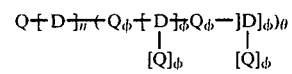

wherein
Q is a nucleophilic residue of an n-valent nucleophilic precursor;
D is a residue of a divinyl ketone;
n is a natural number up to about 5 of the valence of the nucleophilic precursor;
$\phi$ is zero or one; and
$\theta$ is a natural number up to about 10.

Preferably, $\theta$ is from zero to 3. The $\phi$ value may be zero. Most preferably, the polymer linkages are substantially repeating units.

Polyadduct polymers from divinyl ketones prepared with a nucleophilic precursor such as the monoadduct monomers of divinyl ketones of the general formula

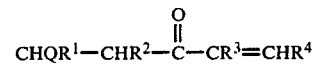

may contain pendant nucleophile residue moieties. The polyadduct polymers with such pendant nucleophilic residue moieties are a preferred class of polyadduct polymers.

The pendant nucleophile residue moieties result from addition involving the remaining vinyl bond of the monoadduct monomer. As such $[D]_\phi$ is therein a pendant nucleophile residue in the foregoing general formula (i.e., $\phi$ of [D] is one), and the $\phi$ of the unbracketed Q is zero, with a pendant [Q] attached solely to the pendant D, with the $\phi$ of the [Q] one. For example, the polyadduct polymer may contain pendant nucleophile groups from the self-addition of the monoadduct monomer made from the compound divinyl ketone and the pendant [Q] from a mono-blocked nucleophile residue of 1-piperazineethaneamine.

The polyadduct polymers may be prepared by polymerization of a polyadduct polymer precursor. The polyadduct polymer precursor may be a monoadduct monomer from a divinyl ketone or may contain another nucleophile. The polyadduct polymer precursor is such that it reacts under conditions sufficient to prepare the polyadduct polymers.

Preferably, the reaction is substantially an addition involving the vinyl bonds of the polyadduct polymer precursor. More preferably therein, substantial amounts of the carbonyl oxygen remain intact.

The most advantageous methods of polymerizing the monoadduct monomers having functionality such as thiol functionality are free radical initiated and base catalyzed. Often gentle heating alone is sufficient. For example, polymerization of monoadduct monomers having sulfinic acid ester functionality is preferably base catalyzed, and polymerization of monoadduct monomers having phosphinic acid ester functionality is preferably carried out without added catalyst.

The polyadduct polymer precursor may result in a polymer with repeating units of a generally straight-chained polyadduct polymer with only small amounts of cross-linking present, especially about 10 percent cross-linking or below, more especially about 5 percent or below and most especially about 1 percent or below.

Thus, it may be desirable to employ a free-radical polymerization inhibitor if the polymerization process may proceed by a process such as a base catalysed polycondensation. Suitable free-radical polymerization inhibitors include compounds such as sodium nitrite, trinitrobenzene or an air/diphenylamine mixture.

The molecular weights of the polyadducts are generally high. Preferably, the number average molecular weight is about 5,000 amu or above, more preferably about 20,000 amu or above and most preferably about 100,000 amu or above.

It is especially preferred that the molecular weight of the polyadducts be such that the desired end use of the polyadducts be accomplished. For example, a cured solid coating of a surface such as an automobile sheet metal component or a glass table top may involve a polyadduct so linked as to be essentially one molecule having a molecular weight limited only by the molecular components and the thickness of the coating and area covered. It may be desired that certain polyadducts be only of a molecular weight sufficient to be effective in their particular application known to the skilled artisan, such as in flame-retardant polymers or applications in liquid systems such as liquid phase flocculants, dewatering of aqueous sewage or of coal.

Base catalyzed polyadduct polymers may benefit from the use of soluble carbonate as the basic catalyst. Such use may keep residual base contamination low, and thus, the polyadducts produced therefrom may have increased thermal stability in comparison to a base catalyzed polyadduct polymer made with the use of a basic catalyst such as NaOH.

The prepared monoadduct monomers are useful in both homopolymerizations and copolymerizations. Homopolymerizations are preferred. Copolymerizations may be employed.

The nucleophilic group may be a carbanion-generating compound, especially with two active hydrogens, each attached to a different carbon. For example, in the case of compounds such as phenols, the reaction preferably occurs on a moiety such as carbon rather than on a moiety such as oxygen.

Thermally stable polyadduct polymers are preferred. Preferably, the thermal stability is measured by differential thermal analysis or by thermogravimetric analysis. Especially preferred values of thermal stability therein are weight loss of less than 10 percent by weight and more especially 5 percent by weight when heated in air to 40° C. at a rate of 2 per minute starting at 20° C.

In addition, tough polyadduct polymers are preferred. Preferably, the toughness is measured by a lap shear test. Especially preferred values of toughness therein are values corresponding to about 500 psi (i.e., about 3447 kPa) or greater and more especially values corresponding to about 1000 psi (i.e., about 6895 kPa) or greater. Such lap shear values may be desirable in adhesion testing.

Examples of such thermally stable, tough polyadduct polymers include polyadduct polymers made from polythiol compounds, especially when made from dithiols having thiol functionality apposite on a lengthy aromatic compound such as biphenyl, diphenyl ether, diphenyl sulfide, diphenyl sulfone and diphenyl ketone. More preferred thermally stable polyadduct polymers include dithiols with the thiol functionality at the para-positions of these compounds. It may be desirable to have as much as 10 mole percent of a compound such as a polyfunctional thiol (e.g., a trithiol) in admixture with the compound such as the dithiol.

In addition, certain bis-nucleophiles give more stable adducts than others. The bis-sulfinic acid adducts have a sulfone structure and are therefore thermally stable. Some diamines give more stable adducts than others. If the diamine is aliphatic and therefore basic, it typically tends to self-catalyze its thermal breakdown. Aromatic diamines are less nucleophilic but the adduct, once formed, is usally more stable. It is generally necessary to make each amino group a mononucleophile in order to prevent cyclization during reaction with the divinyl ketone in order to increase thermal stability. Methyl is a preferred substituent for this purpose. It is possible to have an aliphatic diamine of low basicity. For example, aliphatic diamines such as the following

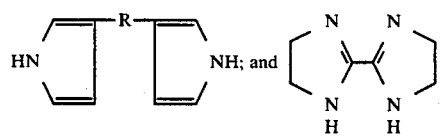

are of low basicity. These, however, may tend to darken in air.

A preferred way of reducing the basicity is to have a thioether in the position beta to the amino group such as found in the secondary amine crown chalconoethers such as N,N'-bis(1-methylethyl)-9-thiabicyclo[3.3.1.]nonane-2,6-diamine. Diamines of this structure typically do not darken in air. The use of a less basic diamine is advantageous also in that there is more effective condensation-type rather than anionic-type polymerization, which typically increases thermal stability.

Fillers and reinforcers may be added. For example, glass fibers may be incorporated into the polyadduct polymer to increase strength and material utilization efficiency.

SPECIFIC EMBODIMENTS

The following examples further illustrate the invention. Percentages are by weight unless otherwise noted.

EXAMPLE 1

A. Monoadduct Preparation

To 12.92 g (0.10 mole) of 1-piperazineethaneamine is added dropwise 6.5 g (0.11 mole) of glacial acetic acid, and the mixture is shaken. Upon cooling to about room temperature, a crystalline solid acetate is formed which includes 1-piperazineethaneamine monoacetate.

To 1.00 g (0.005 mole) of the solid acetate is added 1.0 g (0.012 mole) of 1,4-pentadien-3-one and then 2 ml of methanol. The mixture becomes warm and dissolution begins, and cooling is begun in a refrigerator at about 10° C. and maintained for 5 minutes. The solution is next shaken for 10 minutes. An additional 2 ml of glacial acetic acid is added to help quench the reaction and any excess divinyl ketone and methanol is removed under reduced pressure. The product remains as a dark oil.

B. Polymerization

The dark oil product is exposed to azo-bis-isobutyronitrile, a free radical source, under an dry nitrogen atmosphere and allowed to polymerize overnight. The polymeric solid is dissolved in methanol and precipitated as a hygroscopic solid by the addition of acetone, filtered and dried in an oven for about 1½days. The polymeric yield is 25 percent based on the mass of the assumed 1:1 adduct.

C. Use of Polymer as Flocculant

An aqueous colloid of a spruce wood pulp test mixture (1.1 percent) is effectively flocculated with a 1 percent aqueous mixture of the polymer.

EXAMPLE 2

Three drops of N,N'-bis(1-methylethyl)-9-thiabicyclo[3.3.1.]nonane-2,6-diamine, and one drop of divinyl ketone are mixed at room temperature. A drop of this mixture is applied to an acidized mild steel specimen, and the coating is allowed to cure at room temperature for 12 hours, giving a rust-inhibiting coating to the steel.

EXAMPLE 3

A liquid polythiol of the formula

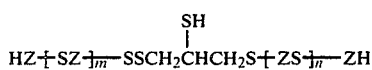

wherein Z is —CH$_2$CH$_2$OCH$_2$CH$_2$S; m is a natural number from about 2 to about 5; n is a natural number from about 2 to about 5; and divinyl ketone are mixed in a respective molar ratio of about 2 with a small amount of tetrabutylammonium hydroxide in methanol (in about a 5 percent methanol solution by weight). Glass is dipped into the mixture and the coating is allowed to cure in air at room temperature for 12 hours, giving a colorless, rubbery coating on the glass. The cross-linked coating is heat resistant to above 250° C.

EXAMPLE 4

Bisphenol A and divinyl ketone are mixed in a nearly equimolar ratio at room temperature in about half their volume of methanol. A catalytic amount of tetrabutylammonium hydroxide is added. Glass is dipped into the mixture and the coating is allowed to cure in air at room temperature for 12 hours, giving a transparent, colorless, hard coating on the glass.

EXAMPLE 5

Biphenyl-4,4'-bis(sulfinic acid) (2.82 g, 0.01 mole) is placed in a small bottle with divinyl ketone (1 g) and t-butyl alcohol (5 ml). The mixture is stirred about 15 hours overnight, closed, at room temperature.

A white precipitate is filtered, suspended in methanol and then acidified with 1 ml of glacial acetic acid. The acidified precipitate is filtered and dried for 24 hours at 22° C. temperature. The biphenylsulfone adduct product solubility: insoluble in water, methanol, acetone and tetrahydrofuran; slightly soluble in methyl ethyl ketone and methyl isobutyl ketone; only partially soluble in dimethylformamide, due to some cross-linking.

EXAMPLE 6

The preparation of Example 6 is repeated at −3° C. Less cross-linking occurs as determined by the foregoing solubility tests.

EXAMPLE 7

The preparation of Example 5 is repeated using methanol in place of t-butyl alcohol. The product is like the polymer of Example 6.

EXAMPLE 8

The preparation of Example 7 is repeated adding 5 ml of pyridine to the reactants as catalyst.

The least amount of cross-linking in comparison with Examples 4–6 occurs. Additional product solubility: insoluble in acetonitrile; soluble in dimethylformamide.

EXAMPLE 9

4,4'-Thiobis(benzenethiol) (0.005 mole) is suspended in 18 ml (1/1) ethanol-water mixture and then divinyl ketone (0.003 mole) is added. The mixture is stirred for 5 minutes at 25° C. No reaction occurs. A total of 0.007 mole of NaOH is then added and the mixture is stirred overnight at 25° C. The bulk of solid product which forms is dissolved in tetrahydrofuran. Gel permeation chromatography of the thiobis(benzenesulfide) adduct of the divinyl ketone product shows a molecular weight of 7723.

COMPARATIVE

The preparation of Example 7 is done, using the disodium salt of the bis(sulfinic acid). No reaction is observed. Thus, the reaction may be inhibited by use of the salt.

We claim:

1. A process for preparing monoadduct monomers of divinyl ketones comprising contacting a nucleophilec precursor and a divinyl ketone under partially neutralized conditions sufficient to cause the nucleophilic precursor to add across a carbon to carbon double bond of the divinyl ketone thereby forming the monoadduct of the divinyl ketone and the nucleophilic precursor.

2. A process for preparing monoadduct monomers of the general formula

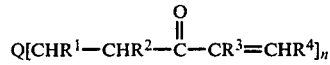

wherein

Q is a component of an n-valent nucleophilic precursor;

R$^1$, R$^2$, R$^3$ and R$^4$ are in each occurrence hydrogen or methyl, and if R$^1$ is hydrogen so is R$^4$; and n is a natural number up to about 5 of the valence of the nucleophilic precursor, comprising contacting a nucleophilic precursor and a divinyl ketone under conditions sufficient to prepare the monoadduct monomer.

3. The process of claim 2 wherein the conditions are partially neutralized.

4. The base-promoted process of claim 3.

5. The process of claim 2 wherein at least $R^2$ and $R^3$ are hydrogen.

6. The process of claim 5 wherein the nucleophilic precursor is monovalent.

7. The process of claim 6 wherein the divinyl ketones comprise the compound divinyl ketone.

8. The process of claim 7 wherein the temperature is about 5° C. or below and divinyl ketone is present in excess.

9. The process of claim 8 wherein the temperature is about 30° C. or below.

10. The process of claim 2 wherein the nucleophilic precursor is a bisulfite anion, sulfinic acid or ester or thiocarboxylic acid ester of about 20 carbon atoms or less per acid and of about 10 carbon atoms or less per esterified group, a compound having exclusive active mercapto functionality of about 20 carbon atoms or less or exclusive active secondary amino functionality of about 20 carbon atoms or less, a phosphite ester of about 10 carbon atoms or less per ester, or an organic bis(phosphonite) of the formula $(R^{10-13}O)_2P\text{-}A\text{-}P(OR^{10-13})_2$ wherein each of $R^{10-13}$ is independently $C_{1-10}$ alkyl and A is ortho-, meta- or para-phenylene, naphthylene, biphenylene, oxybiphenyl, thiobiphenyl, sulfonylbiphenyl, or $C_{7-15}$ arylalkyl.

11. The process of claim 10 conducted in an solvent comprising a $C_{1-4}$ alkyl alcohol or water.

12. The process of claim 11 wherein the nucleophilic precursor comprises the bisulfite anion and the solvent comprises water.

13. The process of claim 11 wherein the nucleophilic precursor comprises a phosphite ester of about 10 carbon atoms per ester or the organic bis(phosphonites) wherein A is para-phosphorous-substituted except for the naphthylyl moiety and each of $R^{10-13}$ is independently $C_{1-4}$ alkyl.

14. The process of claim 13 wherein the phosphite ester comprises trimethyl phosphite or tetramethyl 1,4-phenylenebis(phosphonite).

15. The process of claim 11 wherein the nucleophilic precursor comprises a monovalent mono- or polysecondary amine blocked to a monovalent state crown ether or thioether of about 20 carbon atoms or less.

16. The process of claim 11 wherein the nucleophilic precursor comprises dimethylamine, aziridine, N,N'-bis(1-methylethyl)-9-thiabicyclo[3.3.1]nonane-2,6-diamine monoacetate or 1-piperazineethaneamine monoacetate.

17. The process of claim 16 wherein the nucleophilic precursor comprises 1-piperazineethaneamine monoacetate.

18. The monoadduct monomer composition of claim 18 prepared from contacting $Q(H)_n$ or the equivalent with a divinyl ketone of the formula

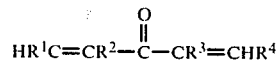

under partially neutralized conditions.

19. The monoadduct monomer composition of claim 18 wherein at least $R^2$ and $R^3$ are hydrogen.

20. The monoadduct monomer composition of claim 19 wherein n is one.

21. The monoadduct monomer composition of claim 20 wherein $R^1$, $R^2$, $R^3$ and $R^4$ are hydrogen.

22. The monoadduct monomer composition of claim 21 wherein the nucleophilic precursor is aziridine, 1-piperazineethaneamine monoacetate, N,N'-bis(1-methylethyl)-9-thiabicyclo[3.3.1]nonane-2,6-diamine monoacetate, trimethylphosphite, tetramethyl 1,4-phenylenebis(phosphonite) or the bisulfite anion.

23. A monoadduct of a divinyl ketone and a nucleophilic precursor, said monoadduct represented by the formula

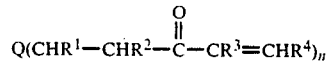

wherein

Q is a component of an n-valent nucleophilic precursor;

$R^1$, $R^2$, $R^3$ and $R^4$ are in each occurrence hydrogen or methyl, and if $R^1$ is hydrogen so is $R^4$; and n is a natural number up to about 5 of the valence of the nucleophile precursor, said nucleophilic precursor being bisulfite anion, a substituted piperazine, an organic bis(phosphonite), or a secondary amine crown chalcono ether.

24. A monoadduct of a divinyl ketone and a nucleophilic precursor, said monoadduct represented by the formula

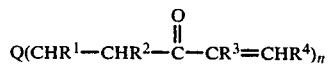

wherein

Q is a component of an n-valent nucleophilic precursor;

$R^1$, $R^2$, $R^3$ and $R^4$ are in each occurrence hydrogen or methyl, and if $R^1$ is hydrogen so is $R^4$; and n is a natural number up to about 5 of the valence of the nucleophilic precursor, said nucleophilic precursor being a bisulfite anion, sulfinic acid or ester or thiocarboxylic acid ester of about 20 carbon atoms or less per acid and of about 10 carbon atoms or less per esterified group, a compound having exclusive active mercapto functionality of about 20 carbon atoms, a phosphite ester of about 10 carbon atoms or less per ester, or an organic bis(phosphonite) of the formula $(R^{10-13}O)_2P\text{-}A\text{-}P(OR^{10-13})_2$ wherein each of $R^{10-13}$ is independently $C_{1-10}$ alkyl and A is ortho-, meta- or para-phenylene, napthylene, biphenylene, oxybiphenyl, thiobiphenyl, sulfonylbiphenyl, or $C_{7-15}$ aralkyl.

* * * * *